US006863786B2

(12) United States Patent
Blinn et al.

(10) Patent No.: US 6,863,786 B2
(45) Date of Patent: Mar. 8, 2005

(54) METHOD AND SYSTEM FOR IMPROVING THE EFFECTIVENESS OF ARTIFICIAL JOINTS BY THE APPLICATION OF GAS CLUSTER ION BEAM TECHNOLOGY

(75) Inventors: Stephen M. Blinn, North Reading, MA (US); Barry M. Zide, Medway, MA (US); Vincent DiFilippo, North Chelmsford, MA (US)

(73) Assignee: Exogenesis Biomedical Technology, Billerica, MA (US)

( * ) Notice: Subject to any disclaimer, the term of this patent is extended or adjusted under 35 U.S.C. 154(b) by 0 days.

(21) Appl. No.: 10/142,137

(22) Filed: May 9, 2002

(65) Prior Publication Data

US 2003/0009233 A1 Jan. 9, 2003

Related U.S. Application Data

(60) Provisional application No. 60/289,737, filed on May 9, 2001.

(51) Int. Cl.[7] .............................................. C23C 14/34
(52) U.S. Cl. .................................... 204/192.34; 216/66
(58) Field of Search ....................... 204/192.34, 298.36; 118/723 CB; 216/66; 156/345.3, 345.39, 345.4

(56) References Cited

U.S. PATENT DOCUMENTS

| | | | | |
|---|---|---|---|---|
| 4,278,493 A | 7/1981 | Petvai | ........................ | 156/643 |
| 4,968,006 A | 11/1990 | Oliver | ........................ | 266/78 |
| 5,123,924 A | 6/1992 | Sioshansi et al. | ............. | 623/16 |
| 5,133,757 A | 7/1992 | Sioshansi et al. | ............. | 623/18 |
| 5,459,326 A | 10/1995 | Yamada | ........................ | 250/398 |
| 5,814,194 A | 9/1998 | Deguchi et al. | ......... | 204/192.1 |
| 5,980,974 A | 11/1999 | Armini et al. | ............. | 427/2.27 |
| 6,207,282 B1 | 3/2001 | Deguchi et al. | ............ | 428/408 |
| 6,231,598 B1 | 5/2001 | Berry et al. | ............... | 623/1.15 |
| 6,331,227 B1 | 12/2001 | Dykstra et al. | .......... | 156/345.1 |
| 6,375,790 B1 | 4/2002 | Fenner | ...................... | 156/345 |
| 2002/0006726 A1 * | 1/2002 | Yamasaki et al. | ........... | 438/689 |
| 2002/0014407 A1 | 2/2002 | Allen et al. | ............ | 204/298.36 |
| 2002/0017454 A1 | 2/2002 | Kirkpatrick | ............ | 204/192.34 |
| 2002/0017455 A1 | 2/2002 | Kirkpatrick et al. | ... | 204/192.34 |
| 2002/0051846 A1 * | 5/2002 | Kirkpatrick et al. | ......... | 427/2.1 |
| 2002/0068132 A1 * | 6/2002 | Skinner et al. | ............. | 427/524 |

FOREIGN PATENT DOCUMENTS

| | | | | |
|---|---|---|---|---|
| JP | 05032424 A | 2/1993 | ........... | C03B/11/08 |
| JP | 08120470 A | 5/1996 | ............ | C23F/4/00 |
| JP | 09040441 A | 2/1997 | ........... | C03C/15/00 |

* cited by examiner

*Primary Examiner*—Steven Versteeg
(74) *Attorney, Agent, or Firm*—Perkins Smith & Cohen; Jerry Cohen; John Hamilton

(57) ABSTRACT

Regardless of the materials used in an artificial joint component design, the present invention applies gas cluster ion beam (GCIB) technology in order to modify the component's surface(s) so as to increase lubrication between contact surfaces, thereby substantially reducing wear debris, osteolysis complications, and accelerated wear failure. The approach of the surface modification comprises an atomic level surface patterning utilizing GCIB to apply a predetermined pattern to the surface(s) of the joint implant to reduce frictional wear at the interface of the surfaces. A reduction in wear debris by GCIB patterning on any surface(s) of a joint prosthesis reduces accelerated failure due to wear and osteolysis and results in a substantial cost savings to the healthcare system, and reduces patient pain and suffering.

6 Claims, 4 Drawing Sheets

US 6,863,786 B2

METHOD AND SYSTEM FOR IMPROVING THE EFFECTIVENESS OF ARTIFICIAL JOINTS BY THE APPLICATION OF GAS CLUSTER ION BEAM TECHNOLOGY

CROSS REFERENCE TO RELATED APPLICATIONS

This application claims priority of U.S. provisional application Ser. No. 60/289,737 entitled "Method and System for Improving the Effectiveness of Artificial Hip Joints by the Application of Gas Cluster Ion Beam Technology", filed May 9, 2001, the provisional application being incorporated herein by reference.

FIELD OF THE INVENTION

This invention relates generally to medical devices such as artificial joints and, more particularly to a method and system for reducing wear in artificial joints using gas cluster ion beam technology.

BACKGROUND OF THE INVENTION

Joint replacement, or arthroplasty, is a surgical procedure in which the diseased parts of a joint are removed and replaced with new, artificial parts. Presently, these artificial joint components are being produced from improved materials such as highly cross-linked polyethylene, metal-on-metal, and ceramic-on-ceramic. After the joint replacement, osteolysis is a major problem and is believed to be due to an inflammatory process brought on by particulate matter or debris dislodged from the implants themselves. In total hip replacements for example, some degree of osteolysis is present in up to 40% of all cases within 10 years of surgery.

Healthy animal joints have an extremely low coefficient of friction and little wear due to cartilage and natural lubricants (e.g. body fluids) formed between joint components. Such minimal friction is difficult to achieve with engineered artificial joints. One problem that contributes to increased wear in artificial joints is a lack of sufficient lubrication between contact surfaces of the implant. The resulting friction produces wear debris that is an important contributor to pathologic tissue response. Therefore, the long-term threat to component failure from a biologic standpoint is this increase in wearing debris associated with osteolysis from a lack of sufficient lubricating matter between surfaces of the implant. The critical initiating sequence involves the interaction between small particulate materials and responding specialized cells that causes destruction of the bone surrounding the implant and loosening of the implant. The number, size, distribution, and type of particulate material are also believed to have an effect on the process.

Designing patterns of channels, cavities or a combination thereof at the contact surface of an implant provides a mechanism to contain an increased volume of lubricating material at the point of contact between implant components. Previous attempts to produce such patterns have used monomer ion beam methods. These monomer ion beams produced deep trenches with rough edges that resulted in increased wear debris as particulate matter from the rough edges flaked off.

In general, surface roughness of artificial joint components can also increase friction between the contact surfaces of the implant and can attribute to wear debris. However, surfaces of artificial joint components having patterns for lubrication purposes are inherently irregular and non-planar and can be difficult to smooth using conventional processing techniques.

Any particulate debris from implanted joints can cause undesirable tissue reaction as well as promote accelerated wearing out and failure of the implants themselves.

It is therefore an object of this invention to provide surface patterning on artificial joint components to provide a more consistent level of lubricating matter between the wearing surfaces.

It is another object of this invention to provide smoothing of a patterned artificial joint component surface.

It is a further object of this invention to provide surface modification of artificial joints by gas cluster ion beams to alleviate the problems associated with component wear and osteolysis.

SUMMARY OF THE INVENTION

The objects set forth above as well as further and other objects and advantages of the present invention are achieved by the invention described hereinbelow.

Several factors have been suggested to minimize the production of wear debris: (1) femoral heads with highly polished cobalt alloy or polished ceramics are believed to be advantageous in minimizing effects of wear on the polyethylene surfaces of the acetabular cups; (2) new highly cross-linked polyethylene acetabular cups are gaining some increased surgical use as a means of decreasing wear and; (3) hard-on-hard implants such as metal-on-metal and ceramic-on-ceramic implants are expected to reduce wear debris.

Regardless of the materials used in the artificial joint designs, the present invention applies gas cluster ion beam (GCIB) technology in order to modify the component's surface, thereby substantially reducing wear debris, osteolysis complications, and accelerated wear failure. The approach of the surface modification comprises an atomic level surface patterning utilizing GCIB to apply a predetermined pattern to the surface(s) of the joint implant and create a new surface configuration that will promote lubricating matter between the implant surfaces to reduce frictional wear at their interface.

A reduction in component wear debris by GCIB patterning on any surface of a joint prosthesis reduces accelerated wear failure and osteolysis that results in a substantial cost savings to the healthcare system, and reduces patient pain and suffering.

For a better understanding of the present invention, together with other and further objects thereof, reference is made to the accompanying drawings and detailed description.

DETAILED DESCRIPTION OF THE PREFERRED METHODS AND EMBODIMENTS

Beams of energetic ions, electrically charged atoms or molecules accelerated through high voltages under vacuum, are widely utilized to form semiconductor device junctions, to smooth surfaces by sputtering, and to enhance the properties of thin films. Gas cluster ions are formed from large numbers of weakly bound atoms or molecules sharing common electrical charges and accelerated together through high voltages to have high total energies. Cluster ions disintegrate upon impact and the total energy of the cluster is shared among the constituent atoms. Because of this energy sharing, the atoms are individually much less energetic than the case of conventional ions or ions not clustered together and, as a result, the atoms penetrate to much shorter depths. Surface sputtering effects are orders of magnitude stronger than corresponding effects produced by conventional ions, thereby making important microscale surface patterning effects possible that are not possible in any other way.

The concept of gas cluster ion beam (GCIB) processing has only emerged over the past decade. Using a GCIB for dry etching, cleaning, and smoothing of materials is known in the art and has been described, for example, by Deguchi, et al. in U.S. Pat. No. 5,814,194, "Substrate Surface Treatment Method", 1998. Because ionized clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459,326, that such individual atoms are not energetic enough to significantly penetrate a surface to cause the residual subsurface damage typically associated with plasma polishing. Nevertheless, the clusters themselves are sufficiently energetic (some thousands of electron volts) to effectively etch, smooth, or clean hard surfaces.

Because the energies of individual atoms within a gas cluster ion are very small, typically a few eV, the atoms penetrate through only a few atomic layers, at most, of a target surface during impact. This shallow penetration of the impacting atoms means all of the energy carried by the entire cluster ion is consequently dissipated in an extremely small volume in the top surface layer during a period on the order of $10^{-12}$ seconds. This is different from the case of ion implantation which is normally done with conventional ions and where the intent is to penetrate into the material, sometimes penetrating several thousand angstroms, to produce changes in the surface properties of the material. Because of the high total energy of the cluster far greater than in the case of bombardment by conventional ions.

Figure 1:
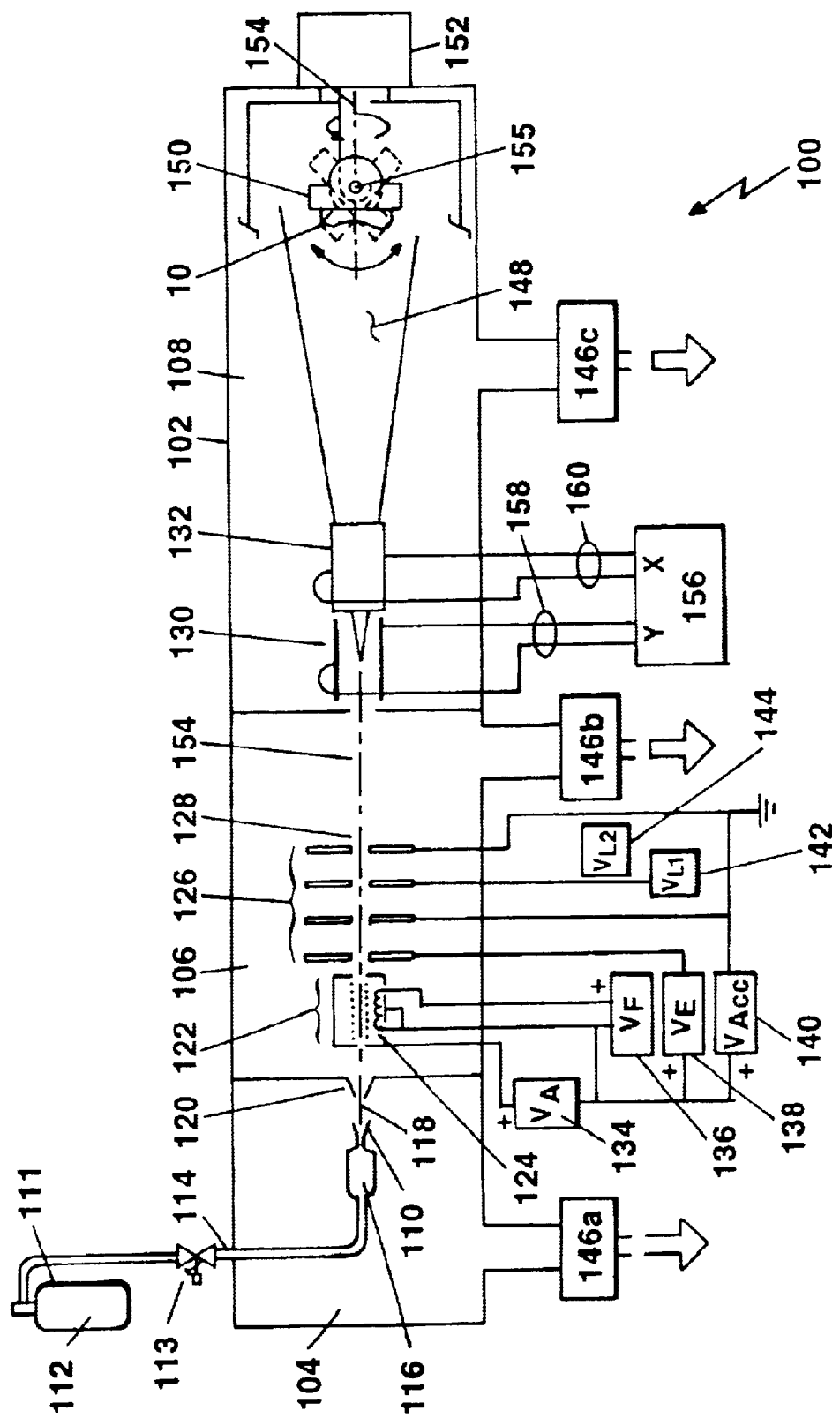
FIG. 1 is a schematic view of a gas cluster ion beam processing system of the present invention.

Reference is now made to FIG. 1 of the drawings which shows the gas cluster ion beam (GCIB) processor 100 of this invention utilized for the surface patterning of an artificial joint component 10. Although not limited to the specific components described herein, the processor 100 is made up of a vacuum vessel 102 which is divided into three communicating chambers, a source chamber 104, an ionization/acceleration chamber 106, and a processing chamber 108 which includes therein a uniquely designed workpiece holder 150 capable of positioning the artificial joint component for uniform patterning by a gas cluster ion beam.

During the patterning method of this invention, the three chambers are evacuated to suitable operating pressures by vacuum pumping systems 146a, 146b, and 146c, respectively. A condensable source gas 112 (for example argon or N2) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, each consisting of from several to several thousand weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable dioxide, and oxygen.

After the supersonic gas jet 118 containing gas clusters has been formed, the clusters are ionized in an ionizer 122. The ionizer 122 is typically an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions to a desired energy (typically from 1 keV to several tens of keV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{ACC}$ to bias a high voltage electrode with respect to the ionizer 122 so as to result in a total GCIB acceleration energy equal to $V_{ACC}$ electron volts (eV). One or more lens power supplies (142 and 144, for example) may be provided to bias high voltage electrodes with potentials ($V_{L1}$ and $V_{L2}$ for example) to focus the GCIB 128.

A medical device such as an artificial joint component 10 (shown in FIG. 1 as an held on a workpiece holder 150, disposed in the path of the GCIB 128. In order for the uniform patterning of the joint component 10 to take place, the workpiece holder 150 is designed in a manner set forth below to appropriately manipulate the joint component 10.

Figure 2:
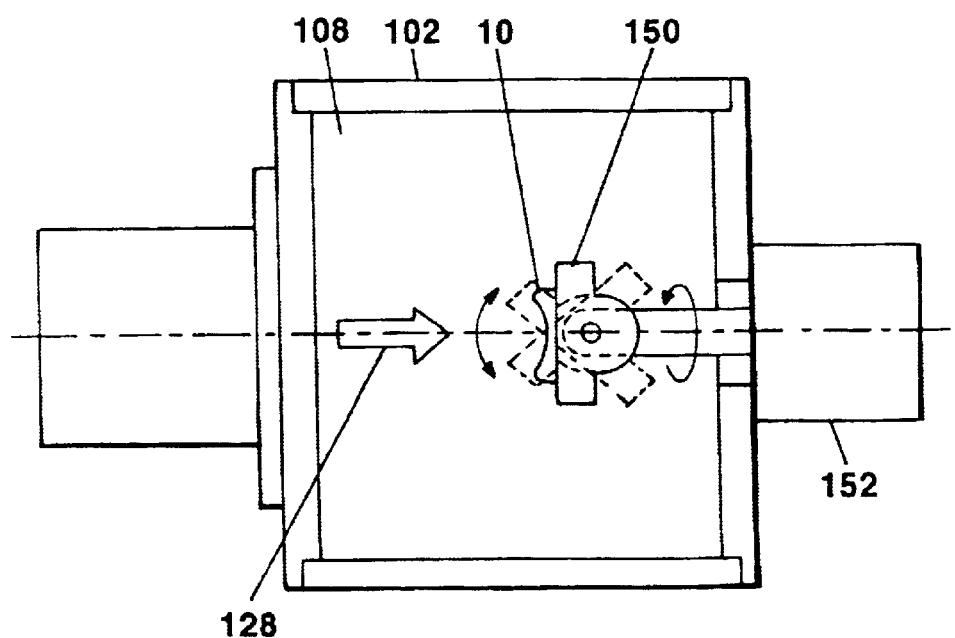
FIG. 2 is an exploded view of a portion of the gas cluster ion beam processing system showing the workpiece holder.

Referring also to FIG. 2, the artificial joint surfaces that are non-planar, that is, may be of a spherical or cup-like configuration, must remain oriented within a specific angle tolerance with respect to the normal beam incidence to obtain paramount patterning of the joint surfaces utilizing GCIB. This requires a joint fixture or workpiece holder 150 with the ability to be fully articulated to orient all non-planar surfaces to be modified within that angle tolerance at a constant exposure level for process optimization and uniformity. Any artificial joint component 10 containing surfaces that would be exposed to the process beam at angles of greater than +/−15 degrees from normal incidence requires manipulation. More specifically, when patterning an artificial joint component 10, the workpiece holder 150 is rotated and articulated by a mechanism 152 located at the end of the GCIB processor 100. The articulation/rotation mechanism 152 preferably permits 360 degrees of device rotation about longitudinal axis 154 and sufficient device articulation about an axis 155 perpendicular to axis 154 to maintain the artificial joint surface to within +/−15 degrees from normal beam incidence.

Preferably, a diffuse beam is utilized when patterning the surface of an artificial joint component. The diffuse beam may be produced using a large beam, or under certain conditions and depending upon the size of the artificial joint component 10, a scanning system may be desirable to produce the patterning desired. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the joint component 10.

When beam scanning over an extended region is not desired, processing is generally confined to a region that is defined by the diameter of the beam. The diameter of the beam at the surface can be set by selecting the voltages ($V_{L1}$ and/or $V_{L2}$) of one or more lens power supplies (142 and 144 shown for example) to provide the desired beam diameter at the workpiece.

A predetermined pattern is formed on a region of the artificial joint component surface during processing by non-uniformly irradiating the surface with the gas cluster ion beam. More specifically, by presenting only certain regions of the surface to the beam results in the reduction of surface volume in such regions due to the sputtering or etching effect of the impacting atoms and less reduction of surface volume in the remaining regions. This causes height variation to occur in the surface plane as the more depressed areas form a series of channels or cavities which are capable of retaining a lubricating matter. In this manner, increased lubrication of between the contact surfaces of the artificial joint components can be achieved, thereby reducing friction and wear debris. Preferably, the majority of the height components and the duration of the gas cluster ion beam processing, depths of several angstroms to several microns may be achieved in the pattern. The pattern itself and the height variations therein can be chosen depending upon the amount of lubrication desired for the artificial joint being implanted. Preferably, a dimpled pattern, similar to the surface of a golf ball, is utilized, but a variety of patterns may be designed for use with the present invention.

In one embodiment of the present invention, a mask is utilized during the irradiation of the surface to form a pattern. Open regions are cut in the mask such that when a region of the surface is covered with the mask only those portions of the surface corresponding to the open regions of the mask are fully exposed to the beam and fully etched. In the portions of the surface blocked by the mask, less surface etching occurs. Alternatively, instead of open regions or in combination thereof, the mask can contain regions of varying thickness, depending upon the surface pattern desired. As the mask is exposed to the beam, the mask becomes etched. The duration of irradiation by the cluster ion beam can be controlled such that over the duration of the processing, regions of the mask having a specific thickness will become fully dissipated and form an aperture through which the surface of the artificial joint component will becomes exposed to the beam. Since these surface is not exposed until after the mask region is etched away, these surfaces are not etched as deeply as surfaces exposed to the beam for the full duration of the processing. In this manner, channels and cavities having a variety of depths can be formed within the same pattern. The masks of the present invention may be produced using a photo-etched metal foil or film, a machined metal foil or film, a polymeric photoresist, or by other materials and forms of patterned masks known from the mask-etching arts. Such a mask is effective when either placed in contact with the surface to be patterned or placed in proximity to the surface to be masked.

Figure 3:
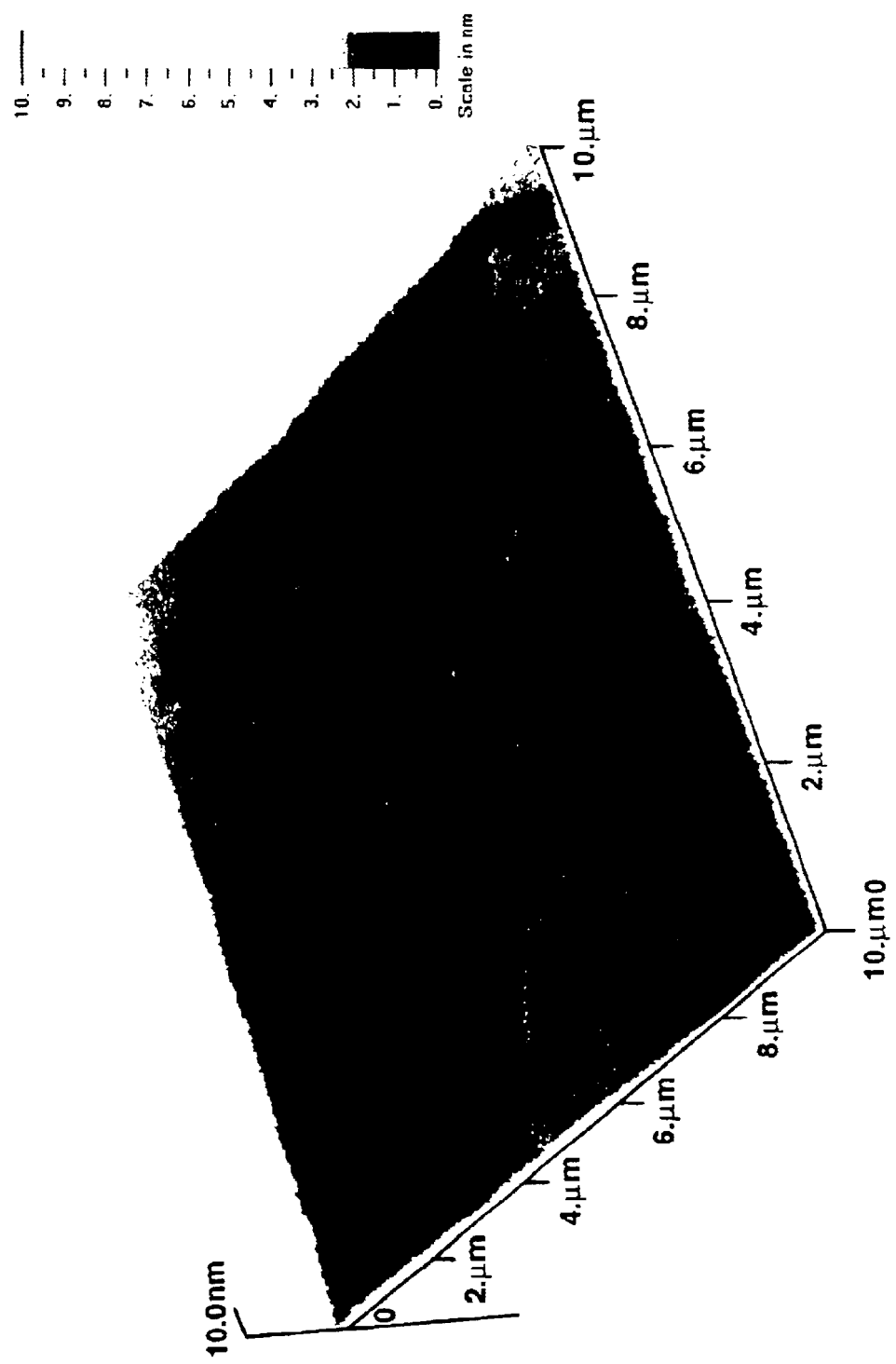
FIG. 3 is an three-dimensional atomic force microscope image showing the surface of an artificial joint component after initial GCIB processing.
Figure 4:
FIG. 4 is a two-dimensional atomic force microscope image showing the surface of an artificial joint component after further GCIB patterning.
Figure 5:
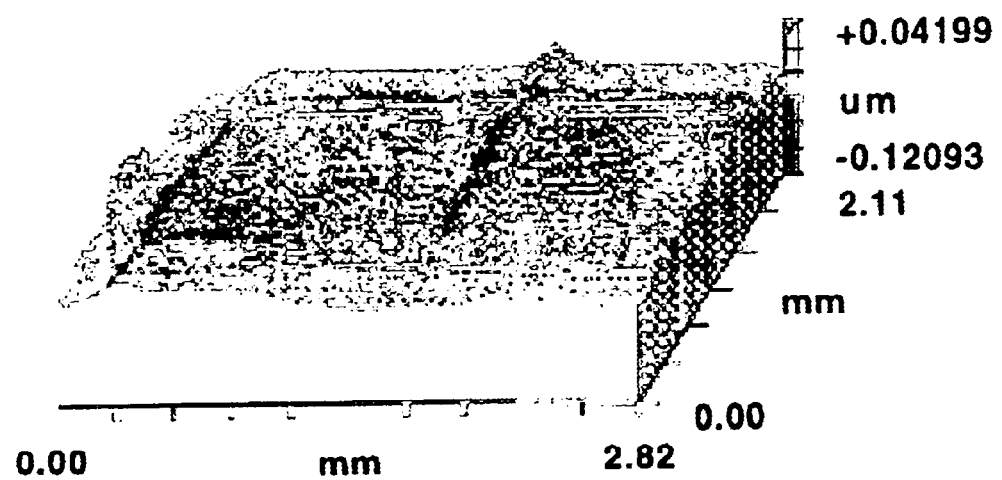
FIG. 5 is a three-dimensional atomic force microscope image of the surface of FIG. 4 showing the surface of an artificial joint component after further GCIB patterning.

As the atomic force microscope (AFM) images shown in FIGS. 3, 4 and 5 demonstrate, it is possible to pattern the surface on artificial joint components 10 utilizing the present invention. FIG. 3 shows a component 10 surface composed of cobalt-chrome after initial GCIB processing with no patterning. The component 10 surface may be patterned with or without this initial processing step, though initial GCIB processing is preferred. FIGS. 4 and 5 show a surface after further GCIB processing where the surface has had a pattern applied without any measurable physical or structural change to the integrity of the material itself. In the embodiment shown in FIGS. 4 and 5, a woven wire screen having approximately 0.2 mm diameter tantalum wire with an approximately 1.2 mm×1.2 mm mesh pitch is used for the mask. The post-GCIB pattern was applied to a depth of approximately 25 angstroms.

As an added benefit, due to the capability of gas cluster ion beam processing to effectively smooth the surface layer of a material, the patterning process itself results in a smoothing of the patterned surface without degrading the pattern formed therein.

Artificial joints generally comprise at least two intermovable components having contacting surfaces in order to mimic the movement of the natural joint. Patterning, as described above, may be utilized on one or more of these surfaces depending upon the amount of lubrication retention desired. Lubricating material may be deposited at the interface of the contacting surfaces and into any patterns etched thereon during assembly and implantation of the artificial joint or subsequent to implantation. Alternatively, the artificial joint components may be implanted and as body fluids form such fluids may naturally be introduced into the pattern after implantation where the fluids will become contained within the channels and cavities of the pattern to provide lubrication for the artificial joint components.

Although the invention has been described with respect to various embodiments, it should be realized this invention is also capable of a wide variety of further and other embodiments within the spirit and scope of the invention.

What is claimed is:

1. A method for modifying a surface of an artificial joint component by gas cluster ion beam processing comprising the steps of:

forming an gas cluster ion beam in a vacuum chamber;

accelerating the gas cluster ion beam;

positioning the surface in the vacuum chamber in the path of the gas cluster ion beam for processing; and non-uniformly irradiating the surface with the gas cluster ion beam to form a pattern in the surface.

2. The method of claim 1 wherein the pattern comprises height variations for retaining a lubricant.

3. The method of claim 2 wherein the lubricant is a body fluid.

4. The method of claim 1 wherein a mask is placed on or in proximity to the surface during the irradiation step to control irradiation patterning, the mask having apertures, thickness variations, or a combination thereof forming a pattern thereon affecting surface modification by the gas cluster ion beam irradiation.

5. The method of claim 4 wherein the mask is a metal foil or film.

6. The method of claim 1 further comprising the step of:

focusing or collimating the gas cluster ion beam to a predetermined small diameter; and wherein the non-uniform irradiation step is performed by controllably positioning the surface relative to the small diameter gas cluster ion beam.

* * * * *